United States Patent [19]  [11] 4,010,269
Renis et al.  [45] Mar. 1, 1977

[54] ANTIVIRAL QUINAZOLINE COMPOSITIONS AND METHODS OF USE

[75] Inventors: Harold E. Renis, Portage; Louis L. Skaletzky, Kalamazoo, both of Mich.

[73] Assignee: The Upjohn Company, Kalamazoo, Mich.

[22] Filed: June 16, 1975

[21] Appl. No.: 586,887

[52] U.S. Cl. .............................................. 424/251
[51] Int. Cl.$^2$ ..................................... A61K 31/505
[58] Field of Search ................................... 424/251

[56] References Cited
UNITED STATES PATENTS
3,900,476   8/1975   Renis et al. .......................... 424/251

*Primary Examiner*—Sam Rosen
*Attorney, Agent, or Firm*—Martin B. Barancik; Roman Saliwanchik

[57] ABSTRACT

2-(1,3-Diaza-2-cycloalken-2-ylamino)quinazolines and substituted compounds are compounded into local and topical compositions for the treatment of viruses.

20 Claims, No Drawings

ANTIVIRAL QUINAZOLINE COMPOSITIONS AND METHODS OF USE

BACKGROUND OF THE INVENTION 2-(1,3-Diaza-2-cycloalken-2-ylamino)quinazolines and substituted quinazolines have been disclosed as having in vitro antiviral activity in Belgian Pat. No. 815,196. However, there is no assertion or suggestion that these compounds have in vivo activity.

It has been discovered that these compounds have significant in vivo antiviral activity as well.

BRIEF SUMMARY OF THE INVENTION

In accordance with this invention, there is disclosed a method for treating viruses in a mammal, said viruses selected from the group consisting of influenza, parainfluenza types 1, 2 and 3, Coxsackie A-21 and rhinovirus, which comprises administering to the mammal an antiviral effective amount of a compound of the formula:

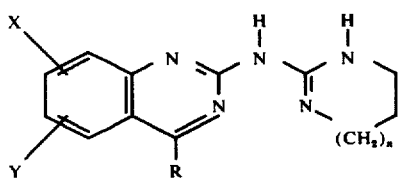

Figure 1 and the non-toxic pharmaceutically acceptable acid addition salts thereof, wherein X and Y are the same or different and are selected from the group consisting of hydrogen, halogen, alkyl of one to six carbon atoms, inclusive, alkoxy of one to six carbon atoms, inclusive; R is alkyl of one to six carbon atoms, inclusive; and $n$ is 0 or 1.

A further aspect of the invention is a pharmaceutical composition adapted for local or topical use comprising a compound of the formula:

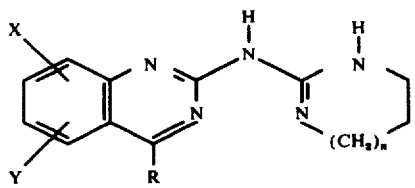

and the non-toxic pharmaceutically acceptable acid addition salts thereof, wherein X and Y are the same or different and are selected from the group consisting of hydrogen, halogen, alkyl of one to six carbon atoms, inclusive, alkoxy of one to six carbon atoms, inclusive; R is alkyl of one to six carbon atoms, inclusive; and $n$ is 0 or 1, in association with a pharmaceutical carrier.

DETAILED DESCRIPTION OF THE INVENTION

The antiviral compounds are readily prepared by the methods of Belgian Pat. No. 815,196, see for example, the description from page four to the start of page thirteen.

Once prepared, the compounds are formulated into pharmaceutical compositions adapted for local or topical administration. The compositions of the invention are presented in solid forms such as powders and freeze-dried preparations as well as in liquid forms such as drops, sprays, mists and aerosols.

Each form used herein contains a concentration of the compound of FIG. 1 as the essential active ingredient such that each unit dose contains an effective amount of the essential active ingredient for antiviral activity. In general, an antiviral effective amount of the compound of FIG. 1 is from about 0.01 to about 50 mg., preferably from about 0.1 to about 20 mg.

These pharmaceutical compositions are particularly useful when applied topically to the oral and related areas such as nasal passages, sinuses, larynx, trachea, bronchi and bronchial tubes. Although the precise mode of antiviral action of the compounds is not known, they demonstrate unexpected pharmacological activity in inhibiting, combatting and destroying viral proliferation and developments.

The delivery mechanism of these compositions can be through the inhaling of a powder manually or through a device such as a Spin-Haler used to deliver disodium cromoglycate, Intal. When using the latter device, the powder can be encapsulated. When employing a liquid composition, the drug can be delivered through a nebulizer, an aerosol vehicle, or through any device which can divide the composition into discrete portions, for example, a medicine dropper or an atomizer of some type.

The compositions are formulated by conventional means. Solid forms of the compositions of the invention, in addition to their concentration of essential active antiviral ingredient, may contain inert materials usually employed in preparing solid pharmaceutical composition such as, for example, binders, excipients, carriers, lubricants, diluents, buffer salts and like inert materials.

The essential active ingredient is mixed with conventional ingredients such as starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size.

Another use of these solid formulations is to use as a base for the liquid formulation.

Liquid formulations, particularly those adapted for nasal drops, sprays, or mists, are prepared in a conventional manner. The essential active ingredient, preferably in a small particle size, for example less than about five microns, is dissolved or dispersed in a small amount of aqueous vehicle or hydroalcoholic vehicle or ethanol or aliphatic alcohol such as oleyl alcohol. Thereafter the solution or suspension is placed into a nebulizer of known types such as a mechanical nebulizer for administration to the infected subject.

As stated previously, the compositions are those adapted for inhalation into the oral and related areas. Compositions for inhalation are of three basic types: (1) a powder mixture preferably micropulverized with particle size, preferably from about 1 to about 5 microns; (2) an aqueous solution to be sprayed with a nebulizer; and (3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the FIG. 1 in water and adding sodium chloride to provide an isotonic solution and buffering to a pH compatible with inhalation. The solutions are dispersed in a spray device or nebulizer and sprayed into the mouth while inhaling.

Suspensions or dispersions can be prepared in the convenient manner and dispersed by appropriate devices. Acid addition salts are preferably employed so as to become solubilized when contacting the target tissue.

Aerosols are prepared by dissolving a compound of the FIG. 1 in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl chlorides. Further suitable liquefied propellants are the fluorinated and fluorochlorinated lower alkanes such as are sold under the trademarks "Freon" and "Genetron". Mixtures of the abovementioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoroethane ("Genetron 142-A"), and monochlorotrifluoromethane ("Freon 13").

The term "unit dosage form", as used in the specification and claims, refers to physically discrete units suitable as unitary dosages for human subject and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are capsules adapted for insufflation, dropperfuls, aerosols with metered discharges, segregated multiples of any of the foregoing, and other forms as herein described.

An effective but non-toxic quantity of the compound is employed in treatment. The dosage of the compound used in treatment depends on the route of administration, e.g., intra nasal, intra bronchial, and the potency of the particular compound. A dose schedule for humans of from about 0.1 to about 20 mg. of the essential active ingredient administered to the oral cavity is effective for antiviral utility. A dose schedule for humans of from about 0.1 to about 5 mg. of the essential active ingredient administered to the nasal passage is effective for antiviral activity. The dosage to be administered can be repeated up to four times daily.

The administration of the compositions of the present invention to humans and animals provides a method for the effective treatment of viral infections. The preferred treatment course is therapeutic. The process can be used for the treatment of the following viruses: influenza, parainfluenza types 1, 2 and 3, Coxsackie A-21 and rhinovirus.

It should be noted that in the examples below the weight of the essential active ingredient is always given in its base form even though the acid addition salt may be named. Additionally, these examples are intended to illustrate the invention rather than limit the inventive concept.

EXAMPLE 1

One hundred packets, each containing 20 mg. of total material and having 1 mg. of active material in each packet, are prepared as follows:

| | |
|---|---|
| 2-(2-Imidazolin-2-ylamino)-4-methylquinazoline hydrochloride | 100 mg. |
| Lactose | 1900 mg. |

The ingredients are mixed, micropulverized, separated, and placed into 100 paper packets.

A human infected with parainfluenza type 1 inhales one packet into each nostril four times daily.

EXAMPLE 2

A powder mixture consisting of 100 mg. of 2-(2-imidazolin-2-ylamino)-4-methylquinazoline and sufficient lactose to make 5 grams of mixture is micropulverized and placed in an insufflation device designed to deliver 50 mg. of powder per dose.

A single dose of the powder is inhaled into the trachea and bronchi by a human infected with equine rhinovirus. This dosage is repeated up to four times daily.

EXAMPLE 3

Twelve grams of an aerosol composition are prepared from the following ingredients:

| | |
|---|---|
| 2-(2-Imidazolin-2-ylamino)-4-methylquinazoline hydrochloride hydrate | 0.10 gm. |
| Freon 12 | 1.44 gm. |
| Freon 114 | 2.16 gm. |
| Water | 8.30 gm. |

The quinazoline is dissolved in the water and chilled to −30° C. and then added to the chilled Freons. The 12 grams of composition are added to a 13 cc plastic coated bottle and capped with a metering valve. The metering valve releases 80 mg. of composition in an aerosol.

The aerosol is inhaled into the trachea of a human infected with an orthomyxovirus every 4 to 6 hours.

EXAMPLE 4

Twelve grams of an aerosol composition are prepared from the following ingredients:

| | |
|---|---|
| 2-(2-Imidazolin-2-ylamino)-4-methylquinazoline | 2.4 gm. |

-continued

| | |
|---|---|
| Freon 12 | 4.8 gm. |
| Freon 114 | 4.8 gm. |

The compound and the chilled Freon are mixed together. The 12 grams of composition are added to a 13 cc plastic coated bottle and capped with a metering valve. The metering valve releases 10 mg. of composition in an aerosol.

One actuation is inhaled into the bronchi of a human every four to 6 hours for the treatment of influenza.

EXAMPLE 5

Six hundred ml. of an aqueous solution containing 2 mg. of 2-(2-imidazolin-2-ylamino)-4-methylquinazoline hydrochloride hydrate per ml. is prepared as follows:

| | |
|---|---|
| 2-(2-Imidazolin-2-ylamino)-4-methylquinazoline hydrochloride hydrate | 1.2 gm. |
| Sodium chloride | 5 gm. |
| Water q.s. | 600 ml. |

The compound and sodium chloride are dissolved in sufficient water to make 600 ml. of solution and sterile filtered.

The solution is placed in nebulizers designed to deliver 0.25 ml. of solution per spray.

0.25 ml. of the solution is inhaled into the mouth and upper trachea of a human for the treatment of a cold caused by a rhinovirus evry 4 to 6 hours.

The treatment is administered to a human infected with equine rhinovirus.

EXAMPLE 6

To the solution of Example 5 is added five ml. of ethanol. The solution is placed in a plastic bottle and a medicine dropper delivers 0.10 ml. of this solution to each nostril of a human having a parainfluenza type 3 infection every 4 to 6 hours.

EXAMPLE 7

The solution of Example 6 is placed in a plastic squeeze bottle container fitted with a dispersing nozzle. A moderate squeeze of the container delivers 0.1 ml. of the solution as a spray.

0.1 ml. of the solution is delivered to each nostril of a human suffering from Coxsackie A-21 virus every 4 to 6 hours.

EXAMPLE 8

After allowing for the differing solubilities of the compounds and the antiviral activity of the particular compound, a suitable quantity of each of the compounds below is substituted for the compound of Examples 1-7 and antiviral activity is observed.

2-[1,4,5,6-tetrahydro-2-pyrimidinyl)amino]-4-methylquinazoline hydrochloride hydrate 2-(2-imidazolin-2-ylamino)-4-butylquinazoline hydrochloride hydrate 2-(2-imidazolin-2-ylamino)-4-hexylquinazoline hydrochloride hydrate 6-chloro-2-(2-imidazolin-2-ylamino)-4-methylquinazoline hydrochloride hydrate 4,6-dimethyl-2-(2-imidazolin-2-ylamino)-quinazoline hydrochloride hydrate 6-methoxy-2-(2-imidazolin-2-ylamino)-4-methylquinazoline hydrochloride hydrate In a similar manner the non-hydrated form of the acid addition salt can be employed. The free base of these compounds can also be employed with facility.

EXAMPLE 9

The compositions of Examples 1-7 and the compounds of Example 8 are used to treat humans infected with rhinovirus, influenza, parainfluenza types 1, 2 and 3 and Coxsackie A-21.

EXAMPLE 10

Hamster nostrils are inoculated with the following viruses — parainfluenza-3, influenza A and equine rhinovirus. 2-(2-Imidazolin-2-ylamino)-4-methylquinazoline hydrochloride hydrate is administered intranasally by nose drops at a dose level of 0.05 ml. per nostril. The concentration of drug varies from 5-40 mg./ml. These nose drops were given seven times during the 24 hour period following virus inoculation. Antiviral activity is determined by comparing virus yields in nose washes from drugtreated hamsters to control hamsters inoculated with virus but treated with drug-absent saline solution.

The results demonstrate reproducible antiviral activity which is drug concentration dependent.

We claim:

1. A pharmaceutical composition suitable for local or topical delivery which comprises about 0.01 to about 50 mg. of a compound of the formula:

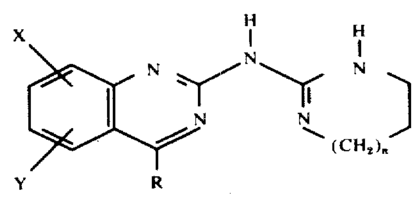

and the non-toxic pharmaceutically acceptable acid addition salts thereof, wherein X and Y are the same or different and are selected from the group consisting of hydrogen, halogen, alkyl of one to six carbon atoms, inclusive, alkoxy of one to six carbon atoms, inclusive; R is alkyl of one to six carbon atoms, inclusive; and *n* is 0 or 1, in association with a pharmaceutically acceptable carrier.

2. A composition in accordance with Claim 1 wherein the composition is an aerosol.

3. A composition in accordance with claim 1 wherein the composition is a powder.

4. A composition in accordance with claim 3 wherein the powder is adapted for insufflation.

5. A composition in accordance with claim 1 wherein the composition is liquid.

6. A composition in accordance with claim 5 wherein the liquid is substantially aqueous.

7. A composition in accordance with claim 1 wherein the compound is 2-(2-imidazolin-2-ylamino)-4-methylquinazoline hydrochloride hydrate.

8. A composition in accordance with claim 1 wherein the compound is 2-(2-imidazolin-2-ylamino)-4-methylquinazoline hydrochloride.

9. A composition in accordance with claim 1 wherein the compound is 2-(2-imidazolin-2-ylamino)-4-methylquinazoline.

10. A method for treating viruses in a mammal, said viruses selected from the group consisting of rhinovirus, influenza, parainfluenza 1, 2 and 3 and Coxsackie A-21 which comprises locally or topically administering to the infected mammal an antiviral effective amount of a compound of the formula:

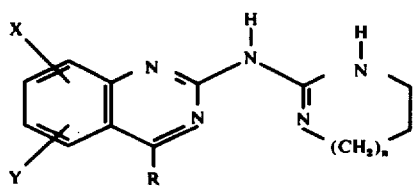

and the non-toxic pharmaceutically acceptable acid addition salts thereof, wherein X and Y are the same or different and are selected from the group consisting of hydrogen, halogen, alkyl of one to six carbon atoms, inclusive, alkoxy of one to six carbon atoms, inclusive; R is alkyl of one to six carbon atoms, inclusive; and $n$ is 0 or 1, in association with a pharmaceutical carrier.

11. A method for treating mammals in accordance with claim 10 wherein the virus is influenza or parainfluenza 1, 2 and 3.

12. A method for treating mammals in accordance with claim 11 wherein the administration route is intranasal.

13. A method for treating mammals in accordance with claim 11 wherein the compound is 2-(2-imidazolin-2-ylamino)-4-methylquinazoline hydrochloride hydrate.

14. A method for treating mammals in accordance with claim 11 wherein the compound is 2-(2-imidazolin-2-ylamino)-4-methylquinazoline hydrochloride.

15. A method for treating mammals in accordance with claim 11 wherein the compound is 2-(2-imidazolin-2-ylamino)-4-methylquinazoline.

16. A method in accordance with claim 10 wherein the virus is a rhinovirus.

17. A method in accordance with claim 16 wherein the rhinovirus is equine rhinovirus.

18. A method is accordance with claim 10 wherein the compound is 2-(2-imidazolin-2-ylamino)-4-methylquinazoline hydrochloride hydrate.

19. A method in accordance with claim 10 wherein the compound is 2-(2-imidazolin-2-ylamino)-4-methylquinazoline hydrochloride.

20. A method in accordance with claim 10 wherein the compound is 2-(2-imidazolin-2-ylamino)-4-methylquinazoline.

* * * * *